United States Patent [19]
Olson

[11] Patent Number: 4,627,963
[45] Date of Patent: Dec. 9, 1986

[54] HEAT ACTIVATED DISPENSER AND METHOD OF DISPENSING A VAPOR THEREFROM

[75] Inventor: Donald M. Olson, Scottsdale, Ariz.

[73] Assignee: LAD Technology, Inc., Phoenix, Ariz.

[21] Appl. No.: 584,826

[22] Filed: Feb. 29, 1984

[51] Int. Cl.$^4$ ................................................. A61L 9/03
[52] U.S. Cl. ........................................ 422/125; 422/5;
422/305; 222/3; 219/271
[58] Field of Search ................... 422/4, 125, 305, 306,
422/5; 239/54, 60; 222/3; 219/271

[56] References Cited
U.S. PATENT DOCUMENTS 2,539,696  1/1951  Morrison ............................. 422/125
2,741,812  4/1956  Tellier ................................. 422/125

FOREIGN PATENT DOCUMENTS 829494   6/1938  France ................................ 422/305
2057884  4/1981  United Kingdom ................ 219/271
2062199  5/1981  United Kingdom .................... 422/4

Primary Examiner—David L. Lacey
Attorney, Agent, or Firm—Harry M. Weiss & Associates

[57] ABSTRACT

A heat activated dispenser is disclosed which is suitable for dispensing into the ambient a variety of materials including medicaments, insect repellants, odor maskants, and the like. The dispenser is formed from compacted diatomite shaped to fit around and receive heat from a heat source such as a light bulb. The diatomite is charged with a vaporizable material which is released into the ambient in a gaseous state when heat is applied to the dispenser. A method of dispensing a vapor into an ambient comprising providing a volume of material having a vaporizable material therein and applying heat thereby causing said vaporizable material to be dispensed into the ambient atmosphere.

20 Claims, 2 Drawing Figures

HEAT ACTIVATED DISPENSER AND METHOD OF DISPENSING A VAPOR THEREFROM

BACKGROUND OF THE INVENTION

This invention relates generally to a heat activated dispenser, and more particularly, to a light bulb heated vapor dispenser.

There are a number of vapor dispensers available for adding to the ambient any one of a number of materials. Vaporizers, for example, boil water and additives in a controlled manner to dispense water vapor and the additives into the ambient to treat various ailments. Aerosol cans provide a timed release of insecticide into the ambient. Metallic cup-like attachments are available which sit on or over a light bulb. The cup provides a reservoir for a volatile material which is boiled off and added to the ambient by the heat from the light bulb.

Although the foregoing dispensers have some utility in specific applications, they also have notable disadvantages or drawbacks. The vaporizer, for example, is bulky, has limited range, requires set-up, and must be stored between uses. The aerosol can is limited in number of materials which can be dispensed (vapor pressure, for example, must be such as to provide a gas at room temperature), has a short effective life, and must usually be used to completion once activated. The cup-like attachment requires the addition of liquid additives, and is potentially dangerous because the metallic cup acquires a high enough temperature to cause skin burns.

Accordingly, a need existed for an improved dispenser which would overcome the problems of the aforementioned dispensers.

It is therefore an object of this invention to provide an improved heat activated vapor dispenser.

It is a further object of this invention to provide an improved light bulb activated vapor dispenser.

BRIEF SUMMARY OF THE INVENTION

The foregoing and other objects of the invention are achieved by a diatomite heat activated vapor dispenser. A volume of diatomite is compacted under high pressure into any shape suitable for accepting heat from a heat source such as a light bulb. A vaporizable material to be dispensed into the ambient is charged into the volume of diatomite, for example, by vacuum impregnation.

DETAILED DESCRIPTION OF PREFERRED EMBODIMENTS

This invention relates to heat activated vapor dispensers; for purposes of illustration only, the invention will be described with reference to specific embodiments adapted to receive heat from a light bulb, but it is not intended that the invention be limited to such specific embodiments.

Figure 1:
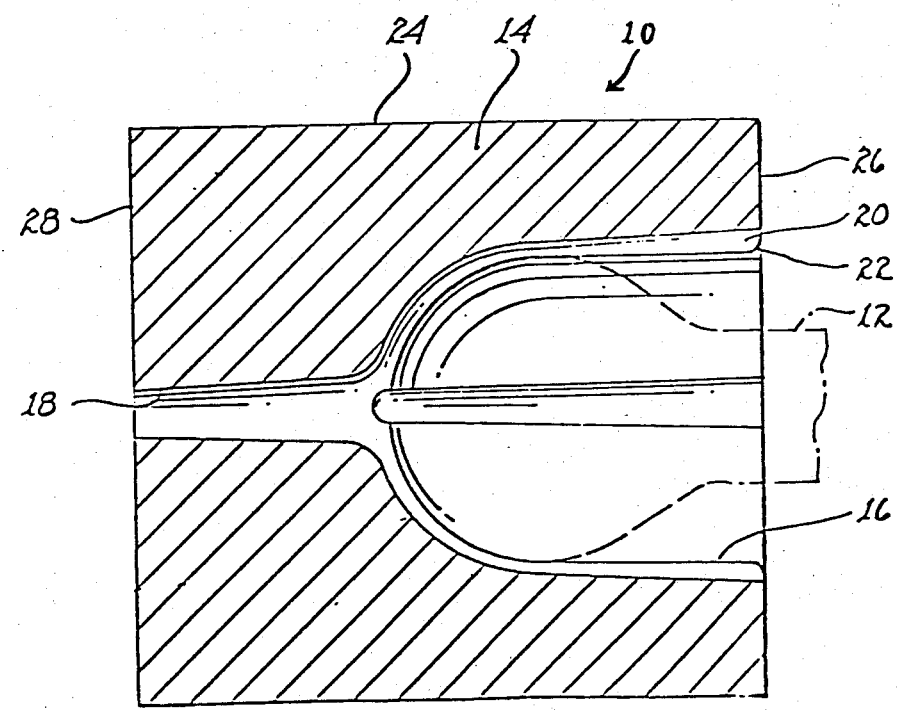
FIG. 1 illustrates, in vertical cross section, a heat activated dispenser adapted for use with a light bulb.

FIG. 1 illustrates, in vertical section, a heat activated dispenser 10 in accordance with the invention. Dispenser 10 is specifically adapted for use with a standard light bulb 12 as a heat source. The dispenser includes a volume 14 of compacted diatomite particles shaped to fit around a heat source, in this illustration the light bulb 12.

Diatomite, also known as diatomaceous earth, is a fine siliceous earth composed mainly of cell walls of diatoms. In this application the diatomite can be used either calcined or uncalcined. The diatomite has a low bulk density of only about 5–10 lbs./cu. ft. Most importantly, however, diatomite has a specific surface of about 215 sq. ft./gm and an absorption capacity of about 3 grams/gram. These properties allow the diatomite dispenser to absorb and hold a large quantity of volatilizable material. In addition, diatomite is relatively inert, has a softening temperature over 1,400° C., and is a poor thermal conductor.

The volume of diatomite particles is preferably formed to the desired shape by high pressure compacting. Volume 14 is formed so that concave interior surface 16 is shaped to operably couple over a standard light bulb, such as a standard 100 watt light bulb, with minimal clearance. Concave interior surface 16 is oriented towards the heat source and an exterior surface 24 is oriented away from the heat source.

The dispenser also preferably includes a vent opening 18 for the escape of gases generated by the heating of the dispenser. The dispenser also preferably includes a plurality of venturi-type channels 20 which extend from the base opening 22 of the dispenser, along the interior concave walls, to the vent opening 18.

Figure 2:
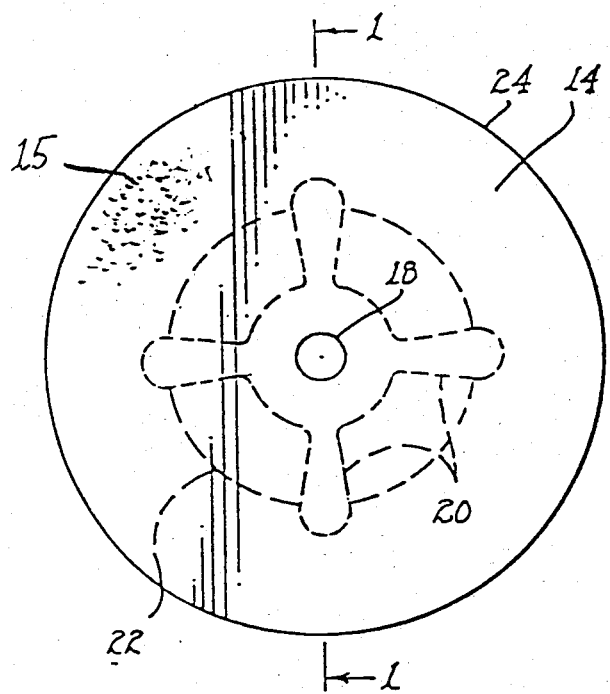
FIG. 2 illustrates, in horizontal section, a preferred embodiment of heat activated dispenser in accordance with the invention.

The positioning of the vent opening and channels is seen more clearly in FIG. 2. The channels 20, in a preferred embodiment are tapered from a relatively wider portion near the base opening to a relatively narrower portion near the vent opening 18. The channels 20 increase the velocity of heated gases flowing around the light bulb and thus impart a distinct upward flow direction to the gases through the dispenser. Four channels 20 are illustrated, but more or less can be utilized, as needed in a particular application.

The volume of diatomite preferably has the shape of a right circular cylinder. The outside 24 and base 26 of the cylinder can be coated with a high temperature paint, epoxy, or the like to inhibit sloughing of particles of diatomite. The interior surface 16 and top surface 28 are left uncoated.

The vaporizable material 15 to be dispensed by the heat activated dispenser is charged to the diatomite. The material can be charged by vacuum impregnation, soaking the diatomite in the material in liquid form, or the like, depending on the nature and characteristics of the material. The material to be dispensed is selected from materials (preferably liquids) having a heat of vaporization such that when sufficient heat is imparted to the dispenser, and therefore to the vaporizable material, the material is readily vaporized. Some materials will require an adjustment of the heat of vaporization, for example by mixing or compounding, to be suitable for certain uses.

Materials 15 can be charged to the diatomite for treating medical ailments, for the dispensing of medicaments, for insect repelling, or eradication, for odor masking, or the like. A quantity of heat is then applied to or conducted into the diatomite to cause a phase transformation and release of the charged material from the volume of diatomite in the gaseous state. The now gaseous material released, by heat activation, from the diatomite, on which it is adsorbed or absorbed, passes through and is accelerated by channels 20 and passes upwardly and outwardly into the ambient through vent opening 18. There will also be a release of the gaseous material or vapors from the outer surface of the volume of compacted diatomite.

Because of its inert and refractory nature, the diatomite is not chemically reactive with the material being dispensed, but rather acts as a binder or source for the material. Also, because of the low thermal conductivity of the diatomite, the outside of the dispenser remains relatively cool and safe to touch.

As a specific but non limiting example, a diatomite heat activated dispenser is charged with perfume. The dispenser is placed on one or more light bulbs in lamps in a room and the lamps are switched on. As the light bulbs heat the interior of the dispenser, perfume is emitted into the room ambient.

Thus it is apparent that there has been provided, in accordance with the invention, a heat activated dispenser that meets the objects and advantages set forth above. The invention has been described and illustrated with respect to certain embodiments thereof, but it is not intended that the invention be limited to these embodiments. Those skilled in the art will recognize, after review of the foregoing description, that variations and modification differing from these embodiments but falling within the spirit of the invention are possible. Other heat sources and shapes of dispensers, for example, are contemplated. All such variations and modifications as fall within the appended claims are therefore considered within the scope of the invention.

I claim:

1. A heat activated vapor dispenser comprising:
   a volume of diatomite compacted under high pressure into a shape constructed so as to accept heat from a heat source and having at least one surface to be oriented towards the heat source, further having at least one surface to be oriented away from the heat source; and
   a vaporizable material to be dispensed, charged into volume.

2. The heat activated dispenser of claim 1 wherein said diatomite is calcined.

3. The heat activated dispenser of claim 1 wherein said at least one surface to be oriented towards the heat source comprises interior walls having a shape of sufficient size to engage a light bulb.

4. The heat activated dispenser of claim 1 wherein said at least one surface to be oriented towards the heat source comprises a concave surface having a radius slightly greater than the size of the heat source.

5. The heat activated dispenser of claim 4 wherein said volume has a shape further comprising a vent opening extending from said at least one surface to be oriented towards the heat source through said volume to said at least one surface to be oriented away from the heat source.

6. The heat activated dispenser of claim 5 wherein said at least one surface to be oriented away from the heat source comprises a right angle circular cylinder.

7. The heat activated dispenser of claim 6 wherein said vent opening extends from said concave surface oriented towards the heat source to an end surface of said right angle circular cylinder.

8. The heat activated dispenser of claim 5 further comprising a plurality of channels formed in said concave surface and extending from a lower extremity of said concave surface to said vent opening.

9. The heat activated dispenser of claim 8 wherein said plurality of channels are tapered, having a greater width at the lower extremity of said concave surface than proximate said vent opening.

10. The heat activated dispenser of claim 1 wherein said vaporizable material comprises any suitable material having a heat of vaporization sufficient to vaporize in response to heat transferred to said volume from a light bulb.

11. A heat activate dispenser comprising:
    a volume of compacted diatomite shaped to have an internal cavity to partially surround a light bulb; and
    a charge of a volatile material vacuum impregnated into said compacted diatomite.

12. The heat activated dispenser of claim 11 wherein said compacted diatomite has an external shape comprising a cylinder.

13. The heat activated dispenser of claim 12 wherein said cylinder is coated with a high temperature material.

14. The heat activated dispenser of claim 11 further comprising a vent opening through said compacted diatomite and coupling said internal cavity and the exterior of said volume.

15. A heat activated dispenser comprising:
    a volume of compacted diatomite having an external surface and having an internal cavity opening at the bottom thereof, said cavity adapted to receive a light bulb;
    a vent opening communicating between said cavity and said external surface;
    a plurality of channels formed in the surface of said cavity and extending from said bottom to said vent opening; and
    a charge of volatile material impregnated in said compacted diatomite.

16. The heat activated dispenser of claim 15 wherein said external surface is generally cylindrical shaped.

17. The heat activated dispenser of claim 16 wherein said cylindrical exterior and said bottom are coated with a high temperature material.

18. The heat activated dispenser of claim 16 wherein said channels are tapered, having a greater width at said bottom than at said vent opening.

19. A heat activated dispenser, comprising:
    a volume of material shaped to accept heat from a light bulb, said volume further comprising a concave surface having a radius slightly greater than the radius of the light bulb, and said volume has a shape further comprising a vent opening extending from the interior extremity of said concave surface through said volume to an exterior surface thereof and further comprising a plurality of channels formed in said concave surface and extending from the lower extremity of said concave surface to said vent opening; and
    a vaporizable material to be dispensed, charged into said volume.

20. The heat activated dispenser of claim 19 wherein said plurality of channels are tapered, having a greater width at said interior extremity of said concave surface than proximate said vent opening.

* * * * *